(12) United States Patent
Schmidt

(10) Patent No.: US 7,003,218 B2
(45) Date of Patent: Feb. 21, 2006

(54) HEATABLE INCUBATOR HOOD AND PROCESS FOR REGULATING THE TEMPURATURE OF AN INCUBATOR HOOD

(75) Inventor: Wolf-Dieter Schmidt, Bad Schwartau (DE)

(73) Assignee: Dräger Medical AG & Co. KGaA, Lübeck (DE)

(*) Notice: Subject to any disclaimer, the term of this patent is extended or adjusted under 35 U.S.C. 154(b) by 0 days.

(21) Appl. No.: 10/677,904

(22) Filed: Oct. 2, 2003

(65) Prior Publication Data
US 2004/0151482 A1 Aug. 5, 2004

(30) Foreign Application Priority Data
Jan. 18, 2003 (DE) ................. 103 01 780

(51) Int. Cl.
*A61G 11/00* (2006.01)
*H05B 1/02* (2006.01)

(52) U.S. Cl. .............. 392/416; 392/418; 219/522; 219/494; 219/505; 600/22

(58) Field of Classification Search ............. 392/416, 392/418, 435; 219/522, 203, 505, 217, 476–478, 219/494; 600/22
See application file for complete search history.

(56) References Cited

U.S. PATENT DOCUMENTS

| | | | | |
|---|---|---|---|---|
| 2,409,083 A | * | 10/1946 | Valverde | 600/22 |
| 2,813,960 A | * | 11/1957 | Egle et al. | 392/435 |
| 2,853,997 A | * | 9/1958 | Scherck | 600/22 |
| 3,299,253 A | * | 1/1967 | Lawson, Jr. | 219/385 |
| 3,529,590 A | * | 9/1970 | Grosholz | 600/22 |
| 3,858,570 A | * | 1/1975 | Beld et al. | 600/22 |
| 4,260,876 A | * | 4/1981 | Hochheiser | 219/497 |
| 5,057,666 A | * | 10/1991 | Takada | 219/203 |
| 5,119,467 A | | 6/1992 | Barsky et al. | |
| 5,496,989 A | * | 3/1996 | Bradford et al. | 219/497 |
| 5,778,689 A | * | 7/1998 | Beatenbough | 62/150 |
| 6,673,007 B1 | * | 1/2004 | Salmon et al. | 600/22 |

FOREIGN PATENT DOCUMENTS

| | | | |
|---|---|---|---|
| CA | 2079947 | * | 4/1994 |
| CA | 2327006 | * | 5/2001 |
| DE | 3717574 | * | 12/1988 |
| GB | 2262439 | * | 6/1993 |
| GB | 2 397 237 | | 3/2005 |
| JP | 10-88935 | * | 4/1998 |

* cited by examiner

Primary Examiner—John A. Jeffery
(74) Attorney, Agent, or Firm—McGlew & Tuttle, P.C.

(57) ABSTRACT

An incubator hood for an incubator for premature and newborn babies as well as to a process for regulating the temperature of an incubator hood are provided. The problem frequently occurring in incubator hoods is that the incubator hoods lead to heat losses at the premature and newborn babies and that water of condensation precipitates on the inside of the incubator in such incubator hoods, and this water of condensation obstructs the view and facilitates the growth of microorganisms in the incubator. This can be counteracted by a heated incubator hood. The comparatively complicated regulation processes, which requires the installation of temperature sensors in the incubator hood is avoided by the use of interior heating wires (1) in which temperature-dependent electric resistors (3), preferably PTC resistors with a nominal response temperature of about 37° C., are arranged. By connecting the heating wires (1) to a power source (2) and by use of an evaluating and control unit, the temperature of the incubator hood can be maintained at about 37° C. and consequently usually above the value of the dew point temperature for the air in the interior of the incubator.

14 Claims, 2 Drawing Sheets

HEATABLE INCUBATOR HOOD AND PROCESS FOR REGULATING THE TEMPURATURE OF AN INCUBATOR HOOD

FIELD OF THE INVENTION

The present invention pertains to an incubator hood for an incubator for premature and newborn babies as well as to a process for regulating the temperature of an incubator hood.

BACKGROUND OF THE INVENTION

Premature and newborn babies who are cared for in an incubator require especially an effective protection from heat losses. The causes for the heat losses can be classified essentially to four different categories, namely, conduction, convection, evaporation and radiation. Conduction means the introduction of heat from the body surface to the bed on which the premature or newborn baby is located. Convention means the release of heat from the body surface to the air flow surrounding the premature or newborn baby in the incubator. Evaporation is defined as the heat of evaporation, which is generated on the body surface of the premature or newborn baby due to the drying air flow in the incubator. Finally, radiation means the heat radiation from the body surface of the premature or newborn baby to the colder surface of the incubator hood. The heat loss caused by radiation accounts for an especially considerable portion of the total heat loss.

It is described in U.S. Pat. No. 5,119,467 how this heat loss generated by heat radiation from the body surface of the premature or newborn baby to the surface of the incubator hood can be reduced. A conductive layer is integrated as a heat radiation source in the incubator hood, and this layer is connected to a temperature regulating circuit. The temperature regulating circuit comprises temperature sensors, whose signals are used to control the electric power source connected to the conductive layer.

The fact that a complicated temperature regulation with temperature sensors and a control unit therefor are necessary was found to be a drawback of the prior-art incubator hood.

SUMMARY OF THE INVENTION

The object of the present invention is to provide an incubator hood for an incubator for premature and newborn babies as well as a process for regulating the temperature of an incubator hood, in which a desired temperature can be maintained with simple and reliable means.

The object is accomplished according to the present invention with an incubator hood for an incubator for premature and newborn babies that is traversed by heating wires, which are connected to a power source. Temperature-dependent electric resistors are arranged in electrically connected to the heating wires. The heating wires are thin and as a result, they reduce the transparency of the incubator hood only slightly, comparably, e.g., to the heating wires that are used to heat the windshields of motor vehicles.

In the process for regulating the temperature of an incubator hood, values in the interior of the incubator are first measured by means of measuring means; these values may be, e.g., the air temperature and the relative humidity of the air, and they are sent to an evaluating and control unit, which forms a value for the dew point temperature in the incubator from the measured values on the basis of physical laws. The temperature of the incubator hood is then regulated by the evaluating and control unit and a correspondingly designed circuit with a power source to a temperature value above the value formed for the dew point temperature by means of heating wires which are connected to the power source and traverse the incubator hood.

The temperature of the incubator hood should advantageously be regulated only when the incubator hood is closed. This can be checked, e.g., with corresponding sensors, and a corresponding signal is then sent to the evaluating and control unit, so that a temperature regulation takes place only if the incubator hood is closed.

It proved to be advantageous to connect the heating wires in parallel. An extensively uniform temperature distribution in space relative to the incubator hood is facilitated especially if the heating wires are distributed uniformly over the incubator hood and only one of the temperature-dependent electric resistors is arranged in electrically connected to each of the heating wires.

By applying a low voltage of a few V, e.g., 30 V, to the heating wires, the incubator hood is heated to the desired temperature. The system formed by the heating wires will hereinafter be called panel heating. The temperature-dependent electric resistors are preferably PTC resistors (positive temperature coefficient), which have been known from numerous industrial applications. PTC resistors are characterized, e.g., by a nominal response temperature of about 37° C. The resistance increases very greatly in the temperature range above this, so that the flow of current and consequently the heating effect caused thereby decreases at a preset voltage that is present on the power source. Temperature regulation of the incubator hood to about 37° C. is thus guaranteed. The temperature of 37° C. is usually above the dew point temperature of the air in the interior of the incubator. The heating effect of the heating wires in the panel heating is coordinated with the temperature characteristic of the PTC resistors being used in a suitable manner.

Besides the reduced heat loss at the premature and newborn baby located in the incubator, the fact that despite the high humidity in the interior of the incubator, no water of condensation is formed on the incubator hood proved to be another advantage of the incubator hood according to the present invention. Water of condensation is always undesirable, because, on the one hand, it obstructs the view from the outside toward the premature and newborn baby in the incubator and, on the other hand, it facilitates the formation or growth of microorganisms in the interior of the incubator.

According to another advantageous embodiment, the incubator hood has limiting surfaces which extend vertically or sloped in relation to the horizontal, so that towels and blankets can be hung over it, but objects are, in general, prevented from being placed on the incubator hood. Covering with a towel or blanket is often useful to ensure a quiet and dark environment for the baby in the incubator. The PTC resistors are arranged such that they are also always covered in case of covering with a towel or a blanket. If, e.g., the incubator hood is designed in the form of a saddle roof, the PTC resistors are advantageously arranged in the ridge of the saddle roof. Heat is thus prevented from accumulating in the interior of the incubator.

Moreover, the fact that the generation of heat in the interior of the incubator is not based on a warm air flow alone any more proved to be a significant advantage of the incubator hood. The velocity of flow and the volume flow of the warm air can be reduced because the heated incubator hood is available as an additional heat source. A reduced velocity of flow leads to the generation of less noise in the incubator. A lower volume flow leads to reduced evaporation on the body surface of the premature and newborn baby. Both effects are desirable.

In a preferred embodiment of the process for regulating the temperature of the incubator hood, heating wires are used, with which temperature-dependent electric resistors, e.g., PTC resistors, are arranged in electrical connection.

The temperature value to which the temperature of the incubator hood is regulated is preferably about 1° C. to 2° C. above the value of the dew point temperature that was formed before by the evaluating and control unit.

The present invention will be explained below as an example based on the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
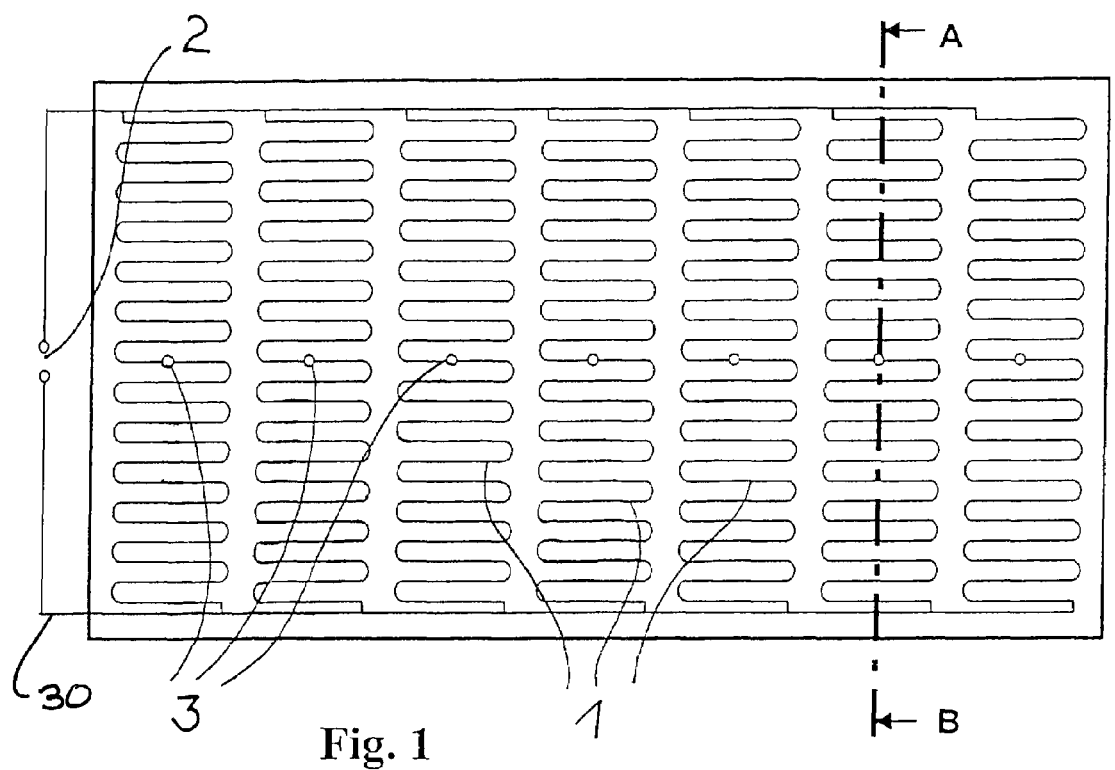
FIG. 1 is a view at right angles from the top of an incubator hood with heating wires and temperature-dependent electric resistors.

Referring to the drawings in particular, FIG. 1 shows a top view of an incubator hood with heating wires 1 and temperature-dependent electric resistors 3. A total of seven heating wires 1 are arranged in parallel. They are wound through the incubator hood in uniform loops. The heating wires 1 are connected to a power source 2 arranged outside the incubator hood. A temperature-dependent electric resistor 3 each is located on the middle path length of each heating wire 1.

Figure 2:
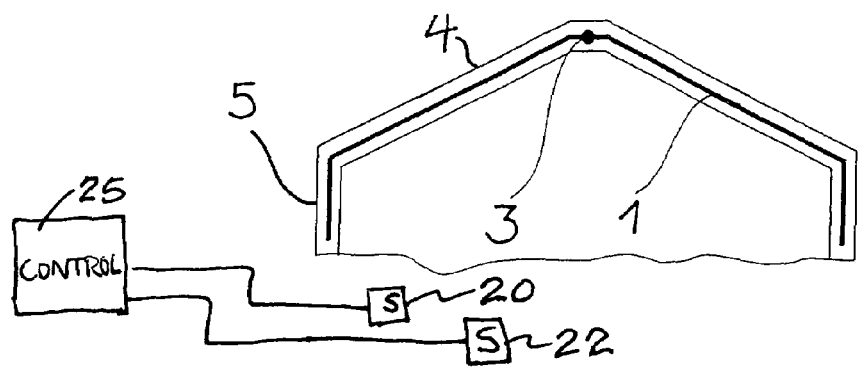
FIG. 2 is a lateral cross section along line A-B showing the incubator hood from FIG. 1.
Figure 3:
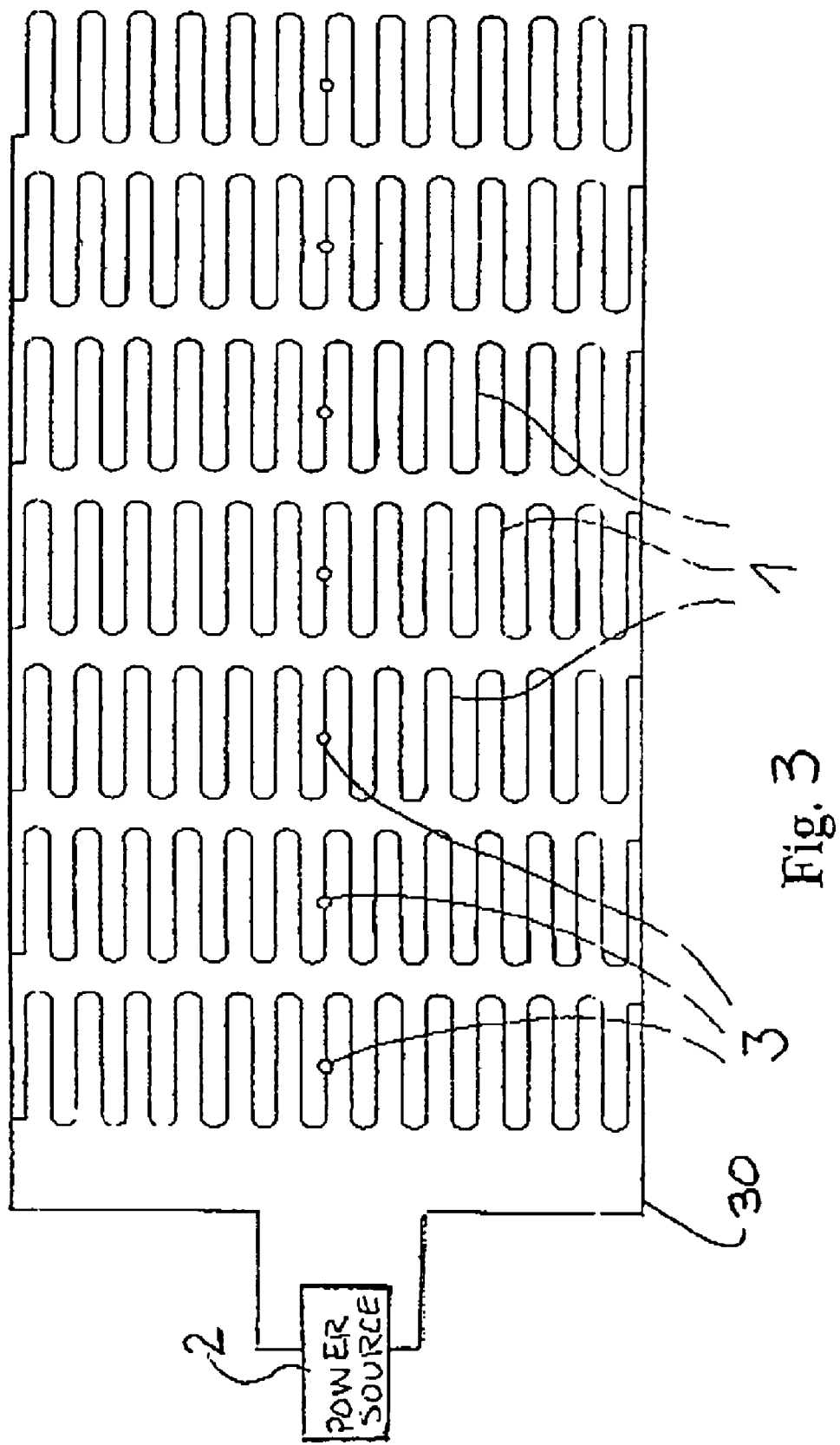
FIG. 3 is a schematic view showing the temperature-dependent heating wires and connected heating wires forming parallel conductive lines.

FIG. 2 shows the incubator hood from FIG. 1 in the lateral cross section along line A-B. The vertically extending limiting surfaces 5 and the limiting surfaces 4 sloped by about 30° against the horizontal in the manner of a saddle roof are shown. One of the temperature-dependent electric resistors 3 is shown on the ridge of the saddle roof.

In the preferred embodiment the heating wires 1 are connected in parallel. One temperature-dependent electric resistors 3 is arranged in electrical connection with each of the heating wires. The temperature-dependent electric resistors 3 are PTC resistors. The heating wires are arranged distributed uniformly in space in the incubator hood.

The incubator hood has vertical limiting surfaces or limiting surfaces extending sloped against the horizontal. The temperature-dependent electric resistors of the incubator hood are used to heat the space of the incubator for premature and newborn babies.

A process is provided for regulating the temperature of the incubator hood. Values in the interior of the incubator are measured with at least one measuring means (a temperature sensor) 20 and are sent to an evaluating and control unit 25, which forms a value for the dew point temperature in the incubator from the measured values. The temperature of the incubator hood is regulated by the evaluating and control unit 25 and a correspondingly designed circuit 30 with the power source 2 to a temperature value above the value formed for the dew point temperature by means of said heating wires 1, which are connected to the power source 2 and traverse the incubator hood.

The air temperature measured by the measuring means (a temperature sensor) 20 with and the relative humidity of the air in the interior of the incubator is measured with a second measuring means 22.

The heating wires 1 in which the temperature-dependent electric resistors 3 are arranged, are used to regulate the temperature. The temperature value to which the temperature of the incubator hood is regulated is about 1° C. to 2° C. above the value formed for the dew point temperature.

While a specific embodiment of the invention has been shown and described in detail to illustrate the application of the principles of the invention, it will be understood that the invention may be embodied otherwise without departing from such principles.

What is claimed is:

1. A process for regulating the temperature of air in an incubator hood, the process comprising the steps of:
    measuring a temperature of the air;
    measuring a relative humidity of the air;
    providing an evaluating and control unit;
    sending temperature and relative humidity measured values to the evaluating and control unit;
    operating the evaluating and control unit to form a value for a dew point temperature in the incubator from the temperature and humidity measured values;
    providing heating wires traversing the incubator hood;
    operating the evaluating and control unit to power the heating wires to heat the incubator hood to a temperature above the dew point temperature;
    arranging temperature-dependent electric resistors in electrical connection with the heating wires and in a position where the temperature of the incubator hood influences the resistance of the temperature-dependent electric resistors; and
    limiting current passing though the heating wires upon the temperature-dependent electric resistors reaching a predetermined temperature.

2. A process in accordance with claim 1, wherein the heating wires are connected in parallel.

3. A process in accordance with claim 1, wherein one of the temperature-dependent electric resistors is arranged in electrical connection with each of the heating wires.

4. A process in accordance with claim 1, wherein the incubator hood has vertical limiting surfaces or limiting surfaces extending sloped with respect to the horizontal.

5. A process in accordance with claim 1, wherein the air temperature is measured with a first measuring means and the relative humidity of the air in the interior of the incubator is measured with a second measuring means.

6. A process in accordance with claim 1, wherein:
    the electric resistors include positive temperature coefficient (PTC) resistors.

7. A process in accordance claim 6, wherein:
    said providing of the heating wires includes distributing the heating wires substantially uniformly in space along an extent of the incubator hood.

8. A process in accordance claim 7, wherein:
    said operating of the evaluating and control unit to heat the incubator hood includes heating the incubator hood to a temperature 1 degree Celsius to 2 degrees Celsius above the dew point temperature.

9. A process in accordance claim 6, wherein:
said operating of the evaluating and control unit to heat the incubator hood includes heating the incubator hood to a temperature 1 degree Celsius to 2 degrees Celsius above the dew point temperature.

10. A process in accordance claim 1, wherein:
said providing of the heating wires includes distributing the heating wires substantially uniformly in space along an extent of the incubator hood.

11. A process in accordance claim 10, wherein:
said operating of the evaluating and control unit to heat the incubator hood includes heating the incubator hood to a temperature 1 degree Celsius to 2 degrees Celsius above the dew point temperature.

12. A process in accordance claim 1, wherein:
said operating of the evaluating and control unit to heat the incubator hood includes heating the incubator hood to a temperature 1 degree Celsius to 2 degrees Celsius above the dew point temperature.

13. A process for regulating the temperature of an incubator hood, the process comprising the steps of:
providing an incubator with an incubator hood defining an interior air space;
providing a plurality of temperature-dependent electric resistors in a position where the temperature of the incubator hood influences the resistance of the temperature-dependent electric resistors;
providing a plurality of heating wires, with pairs of heating wires being electrically connected together via one of the temperature-dependent electric resistors and connected to a power source to form a conductive line, with each conductive line being in contact with the incubator hood, traversing the incubator hood and connected electrically in parallel and with the conductive lines distributed substantially uniformly over an area of the incubator hood;
using a temperature sensor in the air space for measuring a temperature of the air in the interior air space to provide a measured temperature signal;
using a humidity sensor in the air space for measuring a relative humidity of the air in the interior air space to provide a measured humidity signal;
connecting an evaluating and control unit to the humidity sensor, to the temperature sensor and to the power source to control power applied to the parallel conductive lines;
sending the measured temperature signal and the measured relative humidity signal to the evaluating and control unit;
operating the evaluating and control unit to form a value for a dew point temperature in the incubator from the measured temperature signal and the measured relative humidity signal;
operating the evaluating and control unit to apply voltage across the heating wires sufficient to heat the incubator hood to a temperature above the formed value of the dew point temperature;
limiting current passing through each respective conductive line using the respective temperature-dependent electric resistor upon the respective temperature-dependent electric resistor reaching a predetermined temperature based on the temperature of the incubator hood.

14. A process in accordance with claim 13, wherein each temperature-dependent electric resistor comprises a positive temperature coefficient (PTC) resistor and the incubator hood is transparent.

* * * * *